United States Patent [19]

de Wied et al.

[11] 4,256,736

[45] Mar. 17, 1981

[54] PSYCHOPHARMACOLOGICAL PEPTIDES

[75] Inventors: David de Wied, Bilthoven; Hendrik M. Greven, Heesch, both of Netherlands

[73] Assignee: Akzona Incorporated, Asheville, N.C.

[21] Appl. No.: 14,081

[22] Filed: Feb. 22, 1979

[30] Foreign Application Priority Data

Mar. 2, 1978 [NL] Netherlands ................... 7802289

[51] Int. Cl.$^3$ .................... A61K 37/00; C07C 103/52
[52] U.S. Cl. .............................. 424/177; 260/112.5 R
[58] Field of Search ................. 260/112.5 R; 424/177

[56] References Cited

U.S. PATENT DOCUMENTS 4,098,778   7/1978   Li ................................ 260/112.5 R

*Primary Examiner*—Delbert R. Phillips
*Attorney, Agent, or Firm*—Charles A. Wendel; Robert W. Falk; Francis W. Young

[57] ABSTRACT

Novel and biologically useful peptides of the formula: $A_1$-$A_2$-L-Phe-X-L-Thr-L-Ser-$R_1$-Y-L-Ser-$R_2$-L-Thr-L-Pro-L-Leu-L-Val-L-Thr-B are disclosed (together with pharmaceutical compositions comprising a pharmaceutically effective amount of same) wherein:

(a) $A_1$ and $A_2$ each represent an aminoacid residue of the formula $H_2N$-ALK-CO-, where ALK is an alkylidene group with 1 to 6 carbon atoms inclusively;

(b) X is an amino-acid residue selected from the group consisting of L-Met, L-Met(O), L-Met($O_2$) and L-Leu;

(c) $R_1$ and $R_2$ each represent one of the amino-acid residues selected from the group consisting of L-Glu and L-Gln;

(d) Y represents an amino acid residue selected from the group consisting of L-Lys and D-Lys; and (e) B represents one of the amino-acid or peptide moieties selected from L-Leu-OH, D-Leu-OH, L-Leu-L-Phe-OH, L-Leu-L-Phe-L-Lys-OH, L-Leu-L-Phe-D-Lys-OH, L-leucinol and L-MeLeu-OH or a functional derivative thereof; these peptides have psychopharmacological properties capable of accelerating the inhibition of the conditioned flight response, so that they are eminently suitable for the treatment of certain mental disorders in which reduction of the brain function is desired; more particularly the peptides have neuroleptic activity. Peptides of formula (I) wherein one of $R_1$ and $R_2$ is L-Glu and the other L-Gln are preferred, and compositions containing compositions of formula (I) wherein $R_1$ is L-Glu and $R_2$ is L-Gln are especially suitable.

35 Claims, No Drawings

PSYCHOPHARMACOLOGICAL PEPTIDES

BACKGROUND OF THE INVENTION

1. Field of the Invention

The invention described and claimed herein relates to psychopharmacologically-active peptides, methods of preparing such compounds, and pharmaceutical compositions in a form suitable for therapeutic administration containing these peptides. In particular, the present invention relates to novel psychopharmacologically active peptides and peptide derivatives which have been derived from a certain fragment of the hormone β-lipotropin (β-LPH). β-Lipotropin is a polypeptide, consisting of 91 amino-acids, which is formed in the posterior lobe of the hypophysis and shows fat-mobilising activity.

2. Description of the Prior Art and Other Information

Some β-LPH fragments are already known and have been described in the literature. See, for example, the articles in Chem. & Eng. News of Aug. 16, 1976, page 18 and Nov. 15, 1976, page 26.

Thus it is known that the fragment γ-lipotropin, β-LPH-(1-58), possesses fat-mobilising properties just as β-LPH itself. The fragment β-LPH-(41-58), called β-melanotropin, is capable of influencing the pigmentation of the skin by stimulating the melanocytes. The sequence β-LPH-(61-91), called β-endorphin, is known to possess analgesic activity, which just as that of morphine, can be antagonised by naloxone so that the assumption that both morphine and β-endorphin act at the same receptor is logical and obvious.

In the meantime, it has also been found that a certain affinity for the opiate receptor is also shown by smaller peptide fragments of β-endorphin, for example β-LPH-(61-76) (α-endorphin), the fragment β-LPH-(61-69), and the fragment β-LPH-(61-65) (Met-enkephalin). See Nature 258, 577 (1975).

Affinity for the opiate receptor has also been described for the endogenous peptide Leu-enkephalin, [Leu$^{65}$]-β-LPH-(61-65), and for the synthetic D-Ala-Met-enkephalin,[D-Ala$^{62}$]-β-LPH-(61-65). See e.g. Science 194, 330 (1976).

It has furthermore already been ascertained that β-endorphin, β-LPH-(61-91), possesses certain psychopharmacological properties. For example, this peptide inhibits the extinction of the (active) flight response in the well-known pole-climbing test (pole jumping avoidance behavior). This property of β-endorphin cannot be diminished by known morphine antagonists, such as naloxone or naltrexone, so that a conclusion to one skilled in the art that the psychopharmacological activity of β-endorphin is completely independent of the opiate receptor sites in the brains, is certainly justifiable.

Apart from β-endorphin, the smaller peptide fragments derived from this polypeptide, namely α-endorphin, the fragment β-LPH-(61-69) and Met-enkephalin have been shown to inhibit the extinction of the flight response in a similar way.

The peptide γ-endorphin, β-LPH-(61-77), which only differs from α-endorphin through the presence of one extra amino-acid at the C-terminal end, has also proved to possess psychopharmacological activity albeit of a completely different nature than that of α- and β-endorphin. While α-endorphin retarded this extinction of the flight response, γ-endorphin was shown, in contrast, to accelerate the extinction of the flight response. It is remarkable that the mere addition of one amino-acid residue to the C-terminal part of α-endorphin should bring about such a dramatic reversal of the behavioural activity.

Surprisingly, it has now been found that peptides with an amino-acid sequence β-LPH-(62-77) or closely related analogues derived from such a peptide, accelerate the extinction of the flight response to a greater extent than is the case with γ-endorphin. Furthermore, these peptides according to the invention, in contrast to γ-endorphin, do not possess affinity to the opiate receptors.

In U.S. Pat. No. 4,097,471 (Sarantakis) there is disclosed a peptide of the formula H-Tyr-Gly-Gly-Phe-Leu-Thr-Ser-Glu-Lys-Ser-Gln-Thr-Pro-Leu-Val-Thr-OH or a salt thereof. U.S. Pat. No. 4,127,517 (Coy) discloses a peptide of the formula H-Tyr-X-[Gly-Phe-Met-Thr-Ser-Glu-Lys-Ser-Gln-Thr-Pro-Leu-Val-Thr]-Leu-Phe-Lys-Asn-Ala-Ile. U.S. Pat. No. 4,127,518 (Coy) discloses a peptide H-Tyr-X-[Gly-Phe-Met-Thr-Ser-Glu-Lys-Ser-Gln-Thr-Pro-Leu-Val-Thr]-Leu-Y, wherein Y is OH, alkoxy, amine, and salts thereof. U.S. Pat. No. 4,127,519 shows a peptide of a formula analogous to 4,127,518 wherein the Leu moiety outside the bracketed portion is replaced with Leu-Phe moiety. U.S. Pat. No. 4,127,520 also described a peptide analogous to 4,127,518, but replaces 4,127,518's Leu-Y with a Leu-Phe-Lys-Y moiety.

SUMMARY OF THE INVENTION

Surprisingly, novel peptides have been found of the formula:

$$A_1\text{-}A_2\text{-L-Phe-X-L-Thr-L-Ser-}R_1\text{-Y-L-Ser-}R_2\text{-L-Thr-L-Pro-L-Leu-L-Val-L-Thr-B} \quad \text{I}$$
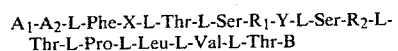

wherein:
(a) A$_1$ and A$_2$ represent each an L-amino-acid residue of the formula H$_2$N-ALK-CO-, wherein ALK is an alkylidene group with 1 to 6 carbon atoms;
(b) X is an amino-acid residue selected from the group consisting of L-Met, L-Met(O), L-Met(O$_2$) and L-Leu;
(c) R$_1$ and R$_2$ each represent one of the amino-acid residues selected from the group consisting of L-Glu and L-Gln;
(d) Y represents an amino-acid residue selected from the group consisting of L-Lys and D-Lys; and
(e) B represents one of the amino-acid- or peptide moieties selected from L-Leu-OH, D-Leu-OH, L-Leu-L-Phe-OH, L-Leu-L-Phe-L-Lys-OH, L-Leu-L-Phe-D-Lys-OH, L-Leucinol and L-MeLeu-OH or a suitable functional derivative thereof.

Especially preferred are the peptides (and compositions containing an effective amount of same) in which one of R$_1$ and R$_2$ L-Glu and the other L-Gln, in particular R$_1$ is Glu and R$_2$ is Gln. By "alkylidene" of one to six carbons it is meant an alkylidene hydrocarbon of one to six carbons unsubstituted by other moieties; the "alkylidene" species may comprise straight-chain or branched-chain species.

The amino-acid residues covered by A$_1$ and/or A$_2$ are for example glycyl, alanyl, valyl, leucyl or isoleucyl, preferably Gly and L-Ala.

DESCRIPTION OF THE PREFERRED EMBODIMENTS

The peptides and peptide derivatives according to the general formula I are prepared in steps each of which are known to those in the art. The methods which are most frequently used for the preparation of the compounds herein referred to may be summarized as follows in three alternative processes:

(a) condensation in the presence of a condensing agent of (1) an amino-acid or peptide containing a free carboxyl group (and in which other reactive groups have been protected) with (2) a compound (amino-acid, peptide or amine) containing a free amino group (and in which other reactive groups have likewise been protected); or (b) condensation of (1) an amino-acid or peptide containing an activated carboxyl group, and in which other reactive groups have optionally been protected, with (2) a compound (amino-acid, peptide or amine) containing a free $NH_2$ group and in which other reactive groups have been protected, or (c) condensation of (1) an amino-acid or peptide containing a free carboxyl group (and in which other reactive groups have been protected) with (2) a compound (amino-acid, peptide or amine) containing an activated amino group (and in which other reactive groups have optionally been protected); after which the protecting groups, if desired, are removed.

Methods of activating the carboxyl group are known to those skilled in the art, and include conversion of same into an acid halide, an azide, anhydride, imidazolide, or an activated ester such as the N-hydroxysuccinimide ester or the p-nitrophenyl ester.

The amino group may be activated by known methods to those in the art, including converting the amino group into a phosphite amide, or by using the "phosphor-azo" method. See for both methods of activating: Houben-Weyl, Methoden der Organischen Chemie, 4th ed., Volume XV/2 (Georg Thieme Verlag), incorporated herein by reference.

The most usual methods for the above-noted condensation reactions are: the carbodi-imide method, the azide method, the mixed anhydride method, and the activated ester method, as described in E. Schröder and K. Lubke, "The Peptides", volume I, 1965 (Academic Press), incorporated herein by reference. The so-called "solid phase" method of Merrifield, described in 85 J. Amer. Chem. Soc. 2149 (1963), also incorporated herein by reference, may furthermore also be used for the preparation of the peptides and peptide derivatives herein described.

The reactive groups which are not to participate in the condensation reaction are effectively protected by suitable so-called "protecting" or "protective" groups which in turn are later readily removed by hydrolysis or reduction. Thus a carboxyl group may be effectively protected by known methods, for example, esterification with at least a stochiometrically effective amount of methanol, ethanol, tertiary butanol, benzyl alcohol or p-nitrobenzyl alcohol, or in the alternative, by conversion by known means into an amide, as for example, described in Houben-Weyl, Methoden der Organischen Chemie, 4th ed., Volume XV/1, page 315 seq. This last protecting group is however very difficult to remove, so that it is recommendable that this group only be used to protect the carboxyl group of the C-terminal amino-acid in the final peptide or the γ-carboxyl group of the glutamic acid. In this case, the the peptides synthesis leads directly to the amide of the peptide according to the general formula (I).

Groups which may effectively protect an amino group are generally suitable acid groups, for example, an acid group derived from suitable aliphatic, aromatic, araliphatic or heterocyclic carboxylic acids (such as acetic acid, benzoic acid, pyridine-carboxylic acid), or an acid group derived from carbonic acid (such as ethoxy-carbonyl, benzyloxy-carboyl, t-butyloxycarbonyl or p-methoxybenzyloxy-carbonyl), or an acid group derived from a sulphonic acid (such as benzene-sulphonyl or p-toluene-sulphonyl). Other groups may also be used, such as substituted or unsubstituted aryl- or aralkyl-groups, for example benzyl and triphenyl-methyl, or groups such as o-nitrophenylsulphenyl or 2-benzoyl-1-methylvinyl. (See Houben-Weyl, Vol. XV/1, page 46 seq.).

It is preferably to protect also the ε-amino group of lysine, and optionally the hydroxyl groups of serine and threonine. This latter protection is however not invariably necessary. The usual protective groups in this connection are a tertiary-butyloxy-carbonyl or a tosyl moiety for the ε-amino group of lysine, and a t-butyl or benzyl moiety for the hydroxyl group of serine and threonine.

The protecting groups may be cleaved by various conventional methods, depending on the nature of the group concerned, for example with the aid of trifluoroacetic acid, or by mild reduction, for example with hydrogen and a catalyst, such as palladium, or with HBr in glacial acetic acid.

Peptides according to the present invention with the amino-acid residue L-Met(O) may be prepared from the corresponding Met-containing peptide by mild oxidation using methods known in the art, for example with dilute hydrogen peroxide or a peracid. Such an oxidation results in a mixture of the S- and R-sulphoxide, which can be resolved into the separate diastereo-isomers by known methods, for example by selective crystallization. The separate diastereoisomers may also be obtained directly by use of L-methionine-S (or R)-sulphoxide in the peptide synthesis.

The sulphone-peptides according to the present invention with the amino-acid residue $Met(O_2)$ may be obtained by oxidation of the corresponding Met-peptide I or by use of methionine-sulphone in the peptide synthesis.

Under the term suitable functional derivatives of the peptides according to the general formula (I) are understood:

(a) salts of the peptides according to the invention, in particular the acid addition salts and metal salts;

(b) esters preferably derived from aliphatic alcohols with one to about eighteen carbon atoms, in particular from alkanols with one to about six atoms, such as methanol, ethanol, propanol, isopropanol, butanol, sec. butyl alcohol, amyl alcohol, iso-amyl alcohol and hexyl alcohol;

(c) amides or mono or di-alkyl-substituted amides, where the alkyl group(s) possess(es) 1 to about 6 carbon atoms; preferably methyl or ethyl;

(d) N-acyl derivatives, derived from an aliphatic carboxylic acid with one to about six carbons; and (e) metal complexes, formed by bringing the peptides herein referred to into contact with a sparingly soluble salt, hydroxide or oxide of a metal, preferably zinc.

Salts may be obtained directly from the reaction milieu in which the peptides are prepared or they may be prepared later by the reaction of the peptide with a base.

The acid addition salts mentioned in (a) above may be obtained directly by isolating the peptide from the desired acid milieu, or the peptide obtained may be converted later into an acid addition salt by reaction of the peptide with an acid such as HCl, HBr, phosphoric acid, sulphuric acid, acetic acid, maleic acid, tartaric acid, citric acid, polyglutamic acid, or carboxymethylcellulose etc.

The metal salts mentioned in (a) above, in particular the alkali metal salts, are obtained by reaction of the peptide with the desired metal base, such as NaOH, $Na_2CO_3$, $NaHCO_3$, etc.

N-acyl derivatives mentioned in (d) above, by which is understood specifically the N-terminal acyl derivatives, are preferably prepared by the use in the peptide synthesis of an amino-acid which already bears the acyl group concerned. This acyl group then also functions as a protective group in the peptide synthesis. In this way, the desired acyl derivatives is prepared directly. It is however also possible to introduce the desired acyl group later, by acylating the peptide in the usual way known to those in the art.

The N-acyl group which is most preferred is the acetyl group.

Esters and amides in (b) and (c) are also preferably prepared by using in the peptide synthesis an amino-acid which already bears the desired ester or amide group; they may however also be prepared later by esterifying the peptide obtained in the usual way known to those in the art, or by converting the same into an amide.

The amides in (c) which are most preferred are the unsubstituted amide; e.g., the mono-methyl- or dimethyl-amide, or the mono-ethyl- or diethyl-amide.

The metal complexes in (e) above may be obtained by bringing the peptide into contact with sparingly soluble metal salts, metal hydroxides or metal oxides. The metal phosphates, metal pyrophosphates and metal polyphosphates are generally used as sparingly soluble metal salts. The metals which may be used in this process are the metals which belong to the "b" subgroups of the Periodic Table, for example cobalt, nickel, copper, iron and preferably zinc, as well as metals from the main groups of the Periodic Table which are capable of forming complexes, such as magnesium and aluminium. The preparation of these metal complexes takes place in the usual way. A metal complex may for example be obtained by addition of the peptide and a sparingly soluble metal salt, metal hydroxide, or metal oxide to an aqueous medium. The metal complex may also be obtained by addition of an alkaline medium to an aqueous solution of the peptide and a soluble metal salt, such that the insoluble peptide-metal hydroxide complex is formed. The metal complex may furthermore be obtained by addition of the peptide, a soluble metal salt and a further soluble salt to an aqueous, preferably alkaline, medium, such that an insoluble peptide-metal salt complex is formed "in situ".

The metal complexes may be used directly without further processing as suspensions, or they may for example be freeze-dried and later resuspended.

The peptides according to general formula I, and the functional derivatives as defined above, accelerate (as already noted above) the extinction of the (active) flight response in rats in the so-called "pole climbing" test to a very considerably extent.

The passive flight behaviour of rats is also considerably reduced on use of the peptides according to the invention.

In addition to the above-noted effects on behaviour, in higher dosages the peptides herein referred to cause a pronounced reduction in ambulation of rats, a surprising effect that could not be observed with α-endorphin or even with γ-endorphin.

The present peptides are furthermore surprisingly active in the so-called "grip test". The rats treated with the peptides according to the invention hang suspended above the floor of the cage with their front paws grasping a pencil for a significantly longer time than rats treated with saline (placebo) or α-endorphin.

This pharmacological profile renders the peptides and peptide derivatives, herein referred to, particularly suitable for use in the treatment of certain mental disorders in which a reduction of the cerebral functions is desired. In particular the present peptides have neuroleptic activity and are thus suitable in the treatment of for example schizophrenic syndromes.

The peptides are used in effective amounts with known carriers, and preferably used in a dosage of 1 μg to 1 mg per kg body weight per day, depending on the form in which they are administered. Humans are preferably treated with a daily dosage of 0,1 mg to about 10 mg, more particularly between 0,5 and 2 mg.

The peptides according to the invention may be administered by either the oral, rectal or the parenteral routes, by means of a pharmaceutically effective carrier known to those in the art. The peptides are preferably used as injectable preparations. For the purposes of injection they are dissolved, suspended or emulsified in a suitable fluid. Mixed with suitable excipients and fillers, the peptides herein referred to may further be provided in a form suitable for oral administration, such as pills, tablets, dragees or capsules. The peptides herein described may furthermore be administered in the form of a suppository or spray.

Particularly valuable preparations are obtained when the peptides herein referred to are provided in a form conferring prolongation of activity. Preferably, the metal complexes are used. These metal complexes may be obtained by bringing the peptides into contact with sparingly soluble metal salts, metal hydroxides or oxides known to those in the art. The metal phosphates, metal pyrophosphates and metal polyphosphates are generally used as sparingly soluble metal salts.

Peptides according to the general formula I which are especially preferred are those peptides in which, $A_1$ and $A_2$ are Gly or L-Ala, X represents L-Met, L-Met(O) or L-Met($O_2$), $R_1$ represents L-Glu, Y represents L-Lys, $R_2$ represents L-Gln, and B represents L-Leu-OH, D-L-Leu-OH or L-Leu-L-Phe-D-Lys-OH, as well as the acid addition salts, lower aliphatic esters and amides thereof.

With respect to the examples below, the following observations and rules are made:

I. If no optical configuration is given, the L-form is implied.

II. The following abbreviations have been used for the protecting or activating groups employed:
Boc=tertiary butyloxycarbonyl
tBu=tertiary butyl
Me=methyl
ONp=p-nitrophenyloxy
Z=benzyloxycarbonyl III. The following abbreviations have been assigned to the solvents or reagents used:
To=toluene
EtOH=ethanol
Bu=butanol
Py=pyridine
Ac=acetic acid
EtOAc=ethyl acetate
Am=amyl alcohol
I.A.N. or IAN=iso-amyl nitrite
DMF=dimethylformamide
THF=tetrahydrofuran
DCCI=dicyclohexylcarbodi-imide
DCHU=dicyclohexylurea
TEA=triethylamine
TFA=trifluoro-acetic acid
Wa=water
N.E.M.=N-ethylmorpholine
HOBt=N-hydroxybenztriazole IV. The following abbreviations have been used for the amino-acid groups:
Met=methionyl
Met(O)=sulphoxide of methionyl
Met(O$_2$)=sulphone of methionyl
Phe=phenylalanyl
Pro=prolyl
Ser=seryl
Lys=lysyl
Thr=threonyl
Glu=glutamyl
Gln=glutaminyl
Gly=glycyl
Val=valyl
Leu=leucyl
Ala=alanyl
MeLeu=N$^\alpha$-methylleucyl Although the invention has been described with respect to the specific embodiments above, numerous variations and modifications will become evident to those skilled in the art, without departing from the scope and spirit of the invention as described above, defined in the appended claims, and as shown in the following examples:

EXAMPLES—STARTING MATERIALS

A. Synthesis of Boc-Gly-Gly-Phe-Met-OH and analogues (1) H-Phe-Met-OMe.HCl 11.83 g of Boc-Phe-Met-OMe (see Biochemistry, 8, 4183 (1969), incorporated herein) is dissolved in 100 ml methylene chloride after which HCl is passed into the solution for about 40 minutes. After evaporation of the solution to dryness, 75 ml ethyl acetate is added, resulting in a precipitate. The solid substance is separated by filtration, washed with petroleum ether, and dried. Melting point 123°–124° C. Rf in To:EtOH (8:2)=0.43 on SiO$_2$.

(2) Boc-Gly-Gly-OH

The procedure followed was that of Tetrahedron 25, 2119 (1976), incorporated herein. Rf in Bu:Py:Ac:Wa (4:0.75:0.25:1)=0.42 on SiO$_2$; decomposition at 125° C.–127° C.

(3) Boc-Gly-Gly-Phe-Met-OMe 4.43 g of Boc-Gly-Gly-OH, A (2) is dissolved in 30 ml DMF and cooled to 0° C., after which 1 equivalent TEA (triethylamine) is added. The mixture is cooled further to about −10° C., after which 1 equivalent (eq) ethyl chloroformate is added and the whole is stirred for about 10 minutes. 6.6 g H-Phe-Met-OMe.HCl (A.1) in 30 ml DMF and 1.1 eq TEA is then added to the mixture, which is stirred for about 30 minutes at about −10° C. and for a further 20 hours at room temperature. After cooling to about −10° C., TEA.HCl is separated by filtration and the filtrate is evaporated to dryness. The residue is dissolved in 235 ml EtOAc and 55 ml water and is subsequently washed with 30% NaCl solution, 0.1 N HCl, 30% NaCl solution, 5% NaHCO$_3$ solution and 30% NaCl solution. The solution is then dried over Na$_2$SO$_4$ filtered and evaporated to dryness. Melting point 100°–101° C.; Rf in CHCl$_3$:CH$_3$OH:Wa (70:30:5)=0.94 on SiO$_2$.

(4) Boc-Gly-Gly-Phe-Met-OH 2.62 g of the peptide obtained in A(3) is dissolved in 30 ml dioxan/H$_2$O-(9:1). After addition of 1.2 eq 2.17 N NaOH, the whole is stirred at room temperature for about 1 hour, after which the pH of the mixture is adjusted to about 6 and it is evaporated to dryness. The residue is subsequently dissolved in 50 ml EtOAc, after which the pH is adjusted to 2 with 1 N HCl. After washing with 30% NaCl (3×), drying over Na$_2$SO$_4$ and filtering, the solution is evaporated to dryness. Rf=0.65. Melting point 97°–98° C.

(5) The following peptides are prepared in an analogous manner:
Boc-Gly-Ala-Phe-Met-OH; Rf=0.72;
Boc-Ala-Gly-Phe-Met-OH; Rf=0.73
Boc-Leu-Gly-Phe-Met-OH; Rf=0.77

The system used in A(4) and A(5) is Bu:Py:Ac:Wa (4:0.75:0.25:1).

B. Synthesis H-Thr-Ser-Glu(OtBu)-Lys(Boc)-OMe and analogues (1) H-Glu(OtBu)-Lys(Boc)-OMe (a) 35.3 g Z-Glu(OtBu)-OH and 27.0 g HOBt are dissolved in 150 ml DMF, after which the mixture is cooled to about −22° C. 29.7 g H-Lys(Boc)-OMe.HCl in 100 ml DMF and 1 eq NEM is then added to the cooled mixture. The pH of the mixture is adjusted to 6.4 with NEM and 23 g DCCI is then added. After stirring for about 15 minutes at about −22° C. and about 12 hours at room temperature, DCHU is separated by filtration and the filtrate is evaporated to dryness.

The residue is dissolved in 400 ml EtOAc and washed consequently with 15% NaCl solution, 5% KHSO$_4$ solution, 5% NaHCO$_3$ solution and 15% NaCl solution. After drying and filtering, the filtrate is evaporated to dryness. The residue is crystallized from ether/petroleum ether (1:2). Yield 86.6%; melting point 54°–56° C.

(b) The peptide obtained in B(1) is dissolved in DMF, after which Pd/C (10%) is added and H$_2$ is passed through until the evolution of CO$_2$ ceases. After filtering, the filtrate is evaporated to dryness. Rf in To:EtOH (8:2)=0.24 on SiO$_2$.

(2) Z-Thr-Ser-N$_2$H$_3$ 38.05 g Z-Thr-Ser-OMe (See Recueil 83, 255, (1964), incorporated herein) is dissolved in 12 ml ethanol, after which 43 ml hydrazine hydrate is added.

After stirring for about 2 hours, the solid substance is separated by filtration, washed with ethanol/ether (1:1) and dried.

Rf in CHCl$_3$:CH$_3$OH:Wa (70:30:5)=0.58 on SiO$_2$; decomposition 215°–216° C.

(3) H-Thr-Ser-Glu(OtBu)-Lys(Boc)-OMe (a) 1.22 g of the hydrazide obtained in B(2) is suspended in 15 ml DMF after which 4.28 ml 2.42 N HCl/DMF is added. The clear solution is cooled to about −20° C. 0.7 ml IAN is then added and the mixture is stirred for about 30 minutes at about −20° C.

1.5 g of the peptide obtained in B(1) in 10 ml DMF is then added. The pH of the reaction mixture is then adjusted to 7.2, and the whole is placed in a refrigerator for about 6 days.

The solvent is then removed by evaporation, the residue is dissolved in EtOAc and the resultant solution is washed. Evaporation to dryness gives a solid substance. Yield 61.9%; melting point 130°–132° C.

(b) In a way similar to that described in B(1)(b) the Z-protected peptide is hydrogenated in methanol with palladium on charcoal as catalyst. Yield 99%; Rf in Bu:Py:Ac:Wa (38:24:8:30)=0.73 on SiO$_2$.

(4) The following protected peptides are obtained in analogous ways:

H-Thr-Ser-Glu(OtBu)-D-Lys(Boc)-OMe

Rf in Bu:Py:Ac:Wa (38:24:8:30)=0.77 on SiO$_2$;

H-Thr-Ser-Gln-Lys(Boc)-OMe

Rf in Bu:Py:Ac:Wa (38:24:8:30)=0.65 on SiO$_2$.

C. Synthesis Z-Ser-R$_2$-Thr-Pro-OH (R$_2$=Glu or Gln)

(1) H-Thr-Pro-OtBu

In the way described in B(1)., 0.33 mol Z-Thr-OH and 0.35 mol H-Pro-OtBu are coupled with the aid of HOBt and DCCI in DMF. Yield 64%; melting point 65°–67° C.

The Z-Thr-Pro-OtBu obtained in this way is hydrogenated in the way described above (see B.3.b.).

Rf in To:EtOH (8:2)=0.10 on SiO$_2$.

(2) H-Gln-Thr-Pro-OtBu 1.36 g H-Thr-Pro-OtBu is dissolved in 10 ml DMF, after which 1.93 g Z-Gln-ONp is added and the reaction mixture is stirred for about 20 hours at room temperature.

After evaporation of the mixture to dryness, the residue is dissolved in EtOAc and washed consecutively with 5% KHSO$_4$ solution, 5% NaHCO$_3$ solution and a saturated NaCl solution. The solution is then dried over Na$_2$SO$_4$ and filtered, and the filtrate is evaporated to dryness.

Melting point 89°–90° C.; yield 59%.

The Z-protected peptide obtained is hydrogenated in DMF in the way described above.

Rf in CHCl$_3$:CH$_3$OH (8:2)=0.08 on SiO$_2$.

(3) Z-Ser-Gln-Thr-Pro-OtBu

In a way analogous to that described in C(1), 20.5 g Z-Ser-OH is coupled with the peptide obtained in C(2) with the aid of DCCI and BOBt.

Yield 70%. Melting point 104°–106° C.

(4) Z-Ser-Gln-Thr-Pro-OH 1.43 g of the peptide obtained in C(3) is stirred in 15 ml 90% TFA at room temperature for about 30 minutes. The mixture is then poured into ether. The solid material is separated by filtration, washed with ether and dried. Yield 90%; melting point 111°–113° C.

Rf in CHCl$_3$:CH$_3$OH:Wa (70:30:5)=0.23 on SiO$_2$.

(5) Z-Ser-Glu(OtBu)-Thr-Pro-OH

H-Thr-Pro-OMe, obtained by coupling Z-Thr-OH and H-Pro-OMe with the aid of the HOBt/DCCI method followed by hydrogenation, is consecutively coupled with Z-Glu(OtBu)-OH and Z-Ser-OH. Both coupling reactions are performed by the HOBt/DCCI method, and after the first coupling of Z-protected peptide obtained is hydrogenated.

The resultant peptide, Z-Ser-Glu(OtBu)-Thr-Pro-OMe, is subsequently saponified by dissolving in dioxan/water (9:1) and addition of 0.2 N NaOH (see A(4)).

Rf in CHCl$_3$:CH$_3$:CH$_3$:OH:Wa (70:30:5)=0.29 on SiO$_2$.

D. Synthesis of H-Leu-Val-Thr-(L or D)-Leu-OtBu (1) H-Thr-Leu-OtBu

In a way corresponding to that described in J.A.C.S. 95, 877 (1973), incorporated herein, Z-Thr-Leu-OtBu is prepared via the HOBt/DCCI coupling method.

Melting point 81.5°–83° C.

The Z-protected dipeptide is then hydrogenated in the way described above.

Yield 100%; Rf in To:EtOH (8:2)=0.20 on SiO$_2$.

(2) H-Thr-D-Leu-OtBu

Obtained by hydrogenation of Z-Thr-D-Leu-OtBu with melting point 89°–92° C.

Rf in To:EtOH (8:2)=0.18 on SiO$_2$.

(3) H-Val-Thr-Leu-OtBu

Coupling of 7.85 g Z-Val-ONp with 5.53 p H-Thr-Leu-OtBu in 160 ml DMF in the way described in C(2) provides Z-Val-Thr-Leu-OtBu in 72% yield.

Melting point 127°–129° C.

Hydrogenation of this Z-protected peptide in methanol gives 9.1 g of an oily product.

Rf in CHCl$_3$:CH$_3$OH (8:2)=0.60 on SiO$_2$.

(4) H-Val-Thr-D-Leu-OtBu

Obtained in a way analogous to that described in D(3).

Rf in CHCl$_3$:CH$_3$OH (8:2)=0.55 on SiO$_2$.

(5) H-Leu-Val-Thr-Leu-OtBu

Coupling of 6.7 g Z-Leu-ONp and 6.1 g of the peptide obtained in D(3), in 160 ml DMF, in the way described in C(2), gives the Z-protected peptide in a yield of 7.7 g (77%). Melting point 153°–155° C. This Z-protected peptide is hydrogenated in methanol. Rf=0.75 on SiO$_2$.

(6) H-Leu-Val-Thr-D-Leu-OtBu

Rf=0.80

(7) H-Leu-Val-Thr-leucinol

Rf=0.50

(8) H-Leu-Val-Thr-MeLeu-OtBu

R$_f$=0.68, prepared in a way analogous to D(5).

Rf in CHCl$_3$:CH$_3$OH:Wa (70:30:5) on SiO$_2$. cl E. Synthesis of Boc-Gly-Gly-Phe-Met-Thr-Ser-Glu(OtBu)-Lys(Boc)-OMe and analogues (1) Boc-Gly-Gly-Phe-Met-Thr-Ser-Glu(OtBu)-Lys(Boc)-OMe 2.4 g Boc-Gly-Gly-Phe-Met-OH, A(4), and 3.15 g H-Thr-Ser-Glu(OtBu)-Lys(Boc)-OMe, B(3), are coupled with the aid of 2 eq HOBt and 1 eq DCCI in the way described in B(1).

After removal of the DCHU by filtration, the filtrate is evaporated to dryness and the residue is crystallized from methanol. Melting point 207°–209° C. (decomposition); yield 61%.

(2) Boc-Gly-Gly-Phe-Met-Thr-Ser-Glu(OtBu)-Lys(Boc)-OH 2.92 g of the peptide obtained in E(1) is dissolved in 30 ml dioxan/water (9:1) after which 14.4 ml 0.217 g NaOH is added to the solution.

The reaction mixture is stirred for 18 minutes at room temperature.

The pH of the mixture is then adjusted to 2 with N HCl. After the addition of about 10 ml water, a solid crystallizes and this is filtered off and dried. Yield 78%; melting point 215°–216° C. (dec.).

Rf in $CHCl_3:CH_3OH:Wa$ (70:30:5)=0.49 on $SiO_2$.

The following are prepared in a corresponding way:

(3) Boc-Ala-Gly-Phe-Met-Thr-Ser-Glu(OtBu)-Lys(Boc)-OH

Rf in $CHCl_3:CH_3OH:Wa$ (70:30:5)=0.52 on $SiO_2$.

(4) Boc-Gly-Ala-Phe-Met-Thr-Ser-Glu(OtBu)-Lys(Boc)-OH

Rf in $CHCl_3:CH_3OH:Wa$ (70:30:5)=0.51 on $SiO_2$.

(5) Boc-Leu-Gly-Phe-Met-Thr-Ser-Glu(OtBu)-Lys(Boc)-OH Rf in $CHCl_3:CH_3OH:Wa$ (70:30:5)=0.54 on $SiO_2$.

(6) Boc-Gly-Gly-Phe-Met-Thr-Ser-Glu(OtBu)-D-Lys(Boc)-OH

Rf in $CHCl_3:CH_3OH:Wa$ (70:30:5)=0.50 on $SiO_2$.

(7) Boc-Gly-Gly-Phe-Met-Thr-Ser-Gln-Lys(Boc)-OH

Rf in $CHCl_3:CH_3OH:Wa$ (70:30:5)=0.40 on $SiO_2$.

F. Synthesis of H-Ser-$R_2$-Thr-Pro-Leu-Val-Thr-(L or D)-Leu-OtBu ($R_2$=Glu(OtBu) or Gln) and analogues (1) H-Ser-Gln-Thr-Pro-Leu-Val-Thr-Leu-OtBu 1.17 g Z-Ser-Gln-Thr-Pro-OH of C(4) is coupled to 930 mg H-Leu-Val-Thr-Leu-OtBu D(5) with the aid of 2 eq HOBt and 1 eq DCCI, according to the method described in B(1). After removal by filtration of the DCHU formed, the filtrate is evaporated to dryness and dissolved in a mixture of sec. butanol and $CHCl_3$ (2:3), after which the solution is washed and evaporated to dryness. The residue is crystallized from DMF/EtOAc (1:20); melting point 210°–212° C. Yield 72%.

The Z-protected peptide obtained is hydrogenated in methanol in the way described above. Yield 86%.

Rf in $CHCl_3:CH_3OH:Wa$ (70:30:5)=0.25 on $SiO_2$.

The following peptides are prepared in a corresponding way:

(2) H-Ser-Glu(OtBu)-Thr-Pro-Leu-Val-Thr-Leu-OtBu, C(5)+D(5).

Rf in $CHCl_3:CH_3OH:Wa$ (70:30:5)=0.35 on $SiO_2$.

(3) H-Ser-Gln-Thr-Pro-Leu-Val-Thr-D-Leu-OtBu, (C(4)+D(6))

Rf in $CHCl_3:CH_3OH:Wa$ (70:30:5)=0.30 on $SiO_2$.

(4) H-Ser-Gln-Thr-Pro-Leu-Val-Thr-Leu-$NHCH_3$ 100 mg of the peptide Z-Ser-Gln-Thr-Pro-Leu-Val-Thr-Leu-OH (see F.5) is dissolved in 2 ml DMF, after which the solution is cooled to about −10° C. 1 eq TEA and 1 eq ethylchloroformate are then added, after which the mixture is stirred for 10 minutes. After addition of an excess of monomethylamine, the mixture is stirred for about 30 minutes at about −10° C. and 2 hours at 0° C., after which the whole is evaporated to dryness. The residue is dissolved in a mixture of sec. butanol and chloroform (2:3), after which the solution is washed, dried, and evaporated to dryness. Yield 65 mg, melting point 223°–225° C.

The Z-protected peptide-monomethylamide obtained is hydrogenated in DMF in the usual way.

Rf in $CHCl_3:CH_3OH:Wa$ (70:30:5)=0.26 on $SiO_2$.

(5) H-Ser-Gln-Thr-Pro-Leu-Val-Thr-Leu-OMe 100 mg of the peptide Z-Ser-Gln-Thr-Pro-Leu-Val-Thr-Leu-OtBu (see F(1)) in 2 ml 90% TFA is stirred for 20 minutes at room temperature. The mixture is then evaporated in dryness and the solid material is filtered off and dried.

The solid (80 mg) is dissolved in DMF and esterified with caesium carbonate and methyl iodide by the method described in J.O.C. 42, 1286 (1977), incorporated herein. The Z-protected peptide methylester is then hydrogenated in DMF in the usual way; yield 45 mg.

Rf in $CHCl_3:CH_3OH:Wa$ (70:30:5)=0.34 on $SiO_2$.

(6) H-Ser-Gln-Thr-Pro-Leu-Val-Thr-Leu-Phe-Lys(Boc)-OtBu 0.992 g Z-Ser-Gln-Thr-Pro-Leu-Val-Thr-Leu-OH of F(5) is coupled to 540 mg H-Phe-Lys(Boc)-OtBu in DMF with the aid of DCCI (1 eq) and HOBt (2 eq). After removal of the DCHU by filtration, the filtrate is evaporated to dryness. The residue is subsequently dissolved in 75 ml sec. butanol/chloroform (2:3) and the solution washed with water, 0.1 N HCl, 5% NaCl solution and water, after which it is dried over $Na_2SO_4$, filtered and the filtrate evaporated to dryness.

Yield of Z-Ser-Gln-Thr-Pro-Leu-Val-Thr-Leu-Phe-Lys(Boc)-OtBu: 1 g; melting point 221°–222° C. (decomposition).

This peptide is hydrogenated in DMF with Pd/C as catalyst in the way described above.

Rf In $CHCl_3:CH_3OH:Wa$ (70:30:5)=0.27 on $SiO_2$.

(7) H-Ser-Gln-Thr-Pro-Leu-Val-Thr-Leu-Phe-OtBu Rf=0.34 on $SiO_2$.

(8) H-Ser-Gln-Thr-Pro-Leu-Val-Thr-MeLeu-OtBu Rf=0.30 on $SiO_2$ (9) H-Ser-Gln-Thr-Pro-Leu-Val-Thr-Leucinol Rf=0.16 on $SiO_2$.

(10) H-Ser-Gln-Thr-Pro-Leu-Val-Thr-Leu-Phe-D-Lys(Boc)-OtBu

Rf=0.48; (7), (8), (9) and (10) being prepared in a way corresponding to that described in F(6). Rf in $CHCl_3:CH_3OH:Wa$ (70:30:5).

EXAMPLE I

Synthesis of
H-Gly-Gly-Phe-Met-Thr-Ser-Glu-Lys-Ser-Gln-Thr-Pro-Leu-Val-Thr-Leu-OH 1.28 g of Boc-Gly-Gly-Phe-Met-Thr-Ser-Glu(Otbu)-Lys(Boc)-OH of E(2) above and 308 mg HOBt were dissolved in 10 ml DMF and the mixture was cooled to about −22° C. 1.05 g H-Ser-Gln-Thr-Pro-Leu-Val-Thr-Leu-OtBu (F(1)) in 5 ml DMF and 1 eq NEM was then added to the cooled mixture. The pH of the mixture was adjusted to 6.5 with NEM and 247 mg DCCI was added. After stirring for 15 minutes at about −22° C., 8 hours at room temperature and finally for 12 hours at 35° C., under $N_2$, the DCHU formed was separated by filtration and the filtrate was washed and dried.

The precipitate formed was washed and dried.

Yield 77%; decomposition at 212°–214° C.

Rf in $CHCl_3:CH_3OH:Wa$ (70:30:5)=0.79 on $SiO_2$.

1.65 g of the protected peptide thus obtained was placed in 30 ml 90% TFA, and a few drops of tert. butyl sulphide were added. The mixture was stirred for 1 hour at room temperature, after which it was poured into ether. The solid thus obtained was separated by filtration and dried. The substance was then dissolved in 30 ml tert. butanol/water (1:1), an ion exchange resin in acetate form (LEWATIT) is added, and the mixture is stirred for about 30 minutes. The ion exchange resin is subsequently removed by filtration, and the filtrate is evaporated to dryness. Yield: 1.2 g.

Rf in Bu:Py:Ac:Wa (2:0.75:0.25:1)=0.26 on $SiO_2$.

The substance is purified by counter-current distribution in the solvent system Bu:Ac:Wa (4:1:5). Yield 680 mg.

EXAMPLE II

Synthesis of H-Gly-Gly-Phe-Met(O)-Thr-Ser-Glu-Lys-Ser-Gln-Thr-Pro-Leu-Val-Thr-Leu-OH 200 mg of the peptide obtained in Example I is dissolved in 20 ml glacial acetic acid, after which 0.08 ml 30% hydrogen peroxide is added. The mixture is stirred for about 1 hour at room temperature, after which 300 mg platinum Black in glacial acetic acid is added to the mixture and the whole is stirred for about a further 15 minutes.

The solid material is separated by filtration and the filtrate is evaporated to dryness.

Yield 190 mg.

The peptide thus obtained is further purified by counter-current distribution chromatography in the solvent system Bu:Ac:Wa (4:1:5).

Yield 150 mg (as acetate).

Rf in Bu:Py:Ac:Wa (2:0.75:0.25:1)=0.20 on $SiO_2$.

EXAMPLE III

Synthesis of H-Gly-Gly-Phe-Met($O_2$)-Thr-Ser-Glu-Lys-Ser-Gln-Thr-Pro-Leu-Val-Thr-Leu-OH 200 mg of the peptide obtained in Example I is introduced into 5 ml water after which 0.025 ml 0.5 M ammonium molybdate, 0.125 ml $HClO_4$ and 0.075 ml 30% hydrogen peroxide are added. The mixture is stirred for about 4 hours at room temperature, after which 5 ml tert. butanol/water (1:1) and an ion exchange resin in acetate form are added. After stirring for about 30 minutes, the ion exchange resin is separated by filtration and the filtrate is evaporated to dryness.

Yield 180 g peptide (in acetate form).

Rf in Bu:Py:Ac:Wa (2:0.75:0.25:1)=0.23 on $SiO_2$.

EXAMPLE IV

The following are prepared in a way corresponding to that described in Example I:

1. H-Ala-Gly-Phe-Met-Thr-Ser-Glu-Lys-Ser-Gln-Thr-Pro-Leu-Val-Thr-Leu-OH
   (E.3+F.1) Rf=0.28
2. H-Gly-Ala-Phe-Met-Thr-Ser-Glu-Lys-Ser-Gln-Thr-Pro-Leu-Val-Thr-Leu-OH
   (E.4+F.1) Rf=0.27
3. H-Leu-Gly-Phe-Met-Thr-Ser-Glu-Lys-Ser-Gln-Thr-Pro-Leu-Val-Thr-Leu-OH
   (E.5+F.1) Rf=0.30
4. H-Gly-Gly-Phe-Met-Thr-Ser-Glu-D-Lys-Ser-Gln-Thr-Pro-Leu-Val-Thr-Leu-OH
   (E.6+F.1) Rf=0.27
5. H-Gly-Gly-Phe-Met-Thr-Ser-Gln-Lys-Ser-Glu-Thr-Pro-Leu-Val-Thr-Leu-OH
   (E.7+F.2) Rf=0.29
6. H-Gly-Gly-Phe-Met-Thr-Ser-Glu-Lys-Ser-Gln-Thr-Pro-Leu-Val-Thr-D-Leu-OH
   (E.2+F.3) Rf=0.33
7. H-Gly-Gly-Phe-Met-thr-Ser-Glu-Lys-Ser-Gln-Thr-Pro-Leu-Val-Thr-Leu-$NHCH_3$
   (E.2+F.4) Rf=0.31
8. H-Gly-Gly-Phe-Met-Thr-Ser-Glu-Lys-Ser-Gln-Thr-Pro-Leu-Val-Thr-Leu-$OCH_3$
   (E.2+F.5) Rf=0.37
9. H-Gly-Gly-Phe-Met-Thr-Ser-Glu-Lys-Ser-Gln-Thr-Pro-Leu-Val-Thr-Leu-Phe-Lys-OH
   (E.2+F.6) Rf=0.24
10. H-Gly-Gly-Phe-Met-Thr-Ser-Glu-Lys-Ser-Gln-Thr-Pro-Leu-Val-Thr-Leu-Phe-OH
    (E.2+F.7) Rf=0.30
11. H-Gly-Gly-Phe-Met-Thr-Ser-Glu-Lys-Ser-Gln-Thr-Pro-Leu-Val-Thr-Leu-Phe-D-Lys-OH
    (E.2+F.10) Rf=0.29.
12. H-Gly-Gly-Phe-Met-Thr-Ser-Glu-Lys-Ser-Gln-Thr-Pro-Leu-Val-Thr-Leucinol
    (E.2+F.9) Rf=0.28
13. H-Gly-Gly-Phe-Met-Thr-Ser-Glu-Lys-Ser-Gln-Thr-Pro-Leu-Val-Thr-MeLeu-OH
    (E.2+F.8) Rf=0.32

All Rf values in Bu:Py:Ac:Wa (2:0.75:0.25:1) on $SiO_2$.

EXAMPLE V

Pole-jumping avoidance behavior

Rats were trained to jump onto a pole within 5 sec. following presentation of the conditioned stimulus (CS) which was a light on top of the cage. Rats which did not jump within 5 sec. received scrambled footshocks (0.2 mA) as the unconditioned stimulus (UCS) until the response was made, or for 30 sec. maximally. 10 trials a day were given in one session with an average intertrial interval of 60 sec. Intervals between trials were 40, 60 and 80 sec. which were presented in a random fashion. Rats were trained for 4 days. Extinction was studied the day following acquisition. During this first post-acquisition session failure to respond within 5 sec. to the CS were not followed by the UCS. All rats were given a 10 trial extinction session. Those animals which made 8 or more avoidances were used for further experimentation. These rats received peptide or placebo (saline) in a volume of 0.5 ml per rat s.c. immediately after completion of the first extinction session. Extinction was studied again 2 and 4 h. later.

| Treatment | Results Extinction (10 trials) | | |
|---|---|---|---|
| | 0 | 2 | 4 |
| γ-Endorphin (reference) | | | |
| 0.03 μg[3] | 8.8 ± 0.3[2] | 6.7 ± 0.8 | 4.0 ± 0.7 |
| 0.1 μg | 9.3 ± 0.3 | 5.5 ± 0.6 | 2.3 ± 0.4 |
| 0.3 μg | 9.0 ± 0.4 | 4.6 ± 0.3 | 0.8 ± 0.4 |
| Saline 0.5 ml | 9.4 ± 0.4 | 8.0 ± 0.5 | 7.8 ± 0.7 |
| α-Endorphin (reference) | | | |
| 0.3 μg | 9.0 ± 0.4 | 8.3 ± 0.3 | 7.8 ± 0.3 |

|  | Results | | |
|---|---|---|---|
|  | Extinction (10 trials) | | |
| Treatment | 0 | 2 | 4 |
| Haloperidol (reference) | | | |
| 0.03 μg | 9.3 ± 0.3 | 6.5 ± 0.7 | 4.0 ± 0.6 |
| 0.1 μg | 9.5 ± 0.4 | 3.0 ± 0.0 | 0.5 ± 0.4 |
| Saline 0.5 ml | 9.8 ± 0.3 | 9.0 ± 0.4 | 7.8 ± 0.5 |
| [Des-Tyr¹]γ-endorphin | | | |
| 0.01 μg | 9.0 ± 0.3 | 6.2 ± 0.4 | 4.2 ± 0.7 |
| 0.1 μg | 8.8 ± 0.4 | 2.8 ± 1.0 | 1.2 ± 0.5 |
| 0.3 μg | 9.3 ± 0.5 | 3.0 ± 0.7 | 1.3 ± 0.5 |
| Saline 0.5 ml | 9.7 ± 0.4 | 9.7 ± 0.4 | 8.7 ± 0.6 |
| [Des-Tyr¹, Met(0)⁵]-γ-endorphin | | | |
| 0.003 μg | 9.0 ± 0.3 | 7.8 ± 0.8 | 4.4 ± 0.9 |
| 0.01 μg | 9.4 ± 0.3 | 4.8 ± 0.7 | 1.4 ± 0.7 |

¹h after injection
²Mean ± S.E.
³Dose per rat s.c.

It is claimed as the invention:

1. A compound of the formula:

$A_1$-$A_2$-L-Phe-X-L-Thr-L-Ser-$R_1$-Y-L-Ser-$R_2$-L-Thr-L-Pro-L-Leu-L-Val-L-Thr-B   (I)

wherein:
(a) $A_1$ and $A_2$ each represent an L-amino-acid residue of the formula $H_2N$-ALK-CO-, wherein ALK is an alkylidene group with 1 to 6 carbon atoms;
(b) X is an amino-acid residue selected from the group consisting of L-Met, L-Met(O), L-Met($O_2$) and L-Leu;
(c) $R_1$ and $R_2$ each represent one of the amino-acid residues selected from the group consisting of L-Glu and L-Gln;
(d) Y represents an amino-acid residue selected from the group consisting of L-Lys and D-Lys; and
(e) B represents one of the amino-acid- or peptide-moieties selected from L-Leu-OH, D-Leu-OH, L-Leu-L-Phe-OH, L-Leu-L-Phe-L-Lys-OH, L-Leu-L-Phe-D-Lys-OH, L-leucinol and L-MeLeu and functional derivatives of said compound selected from the group consisting of pharmaceutically acceptable salts addition salts, pharmaceutically acceptable metal salts, aliphatic esters containing up to about eighteen carbon atoms, unsubstituted amides, amides substituted with alkyl group (s) containing up to about six carbon atoms, N-acyl derivatives wherein the aliphatic carboxylic acid group has from one to about six carbon atoms, and pharmaceutically acceptable metal complexes.

2. The compound of claim 1 wherein $A_1$ is selected from the group consisting of H-Gly and H-L-Ala.

3. The compound of claim 1 wherein $A_2$ is selected from the group consisting of H-Gly and H-L-Ala.

4. The compound of claim 1 wherein B is selected from the group consisting of L-Leu-OH, D-Leu-OH and L-Leu-L-Phe-D-Lys-OH.

5. The compound of claim 1 wherein X is selected from the group consisting of L-Met, L-Met(O), and L-Met($O_2$).

6. The compound of claim 1 wherein $R_1$ is L-Glu and $R_2$ is L-Gln.

7. The compound of claim 1 wherein Y is L-Lys.

8. The compound of claim 1 wherein $A_1$ and $A_2$ are H-Gly, X is L-Met, $R_1$ is L-Glu, $R_2$ is L-Gln, Y is L-Lys and B is L-Leu-OH.

9. The compound of claim 1 wherein $A_1$ and $A_2$ are H-Gly, X is L-Met(0), $R_1$ is L-Glu, $R_2$ is L-Gln, Y is L-Lys and B is L-Leu-OH.

10. The compound of claim 1 wherein $A_1$ and $A_2$ are H-Gly, X is L-Met($O_2$), $R_1$ is L-Glu, $R_2$ is L-Gln, Y is L-Lys and B is L-Leu-OH.

11. The compound of claim 1 wherein $A_1$ and $A_2$ are H-Gly, X is L-Met, $R_1$ is L-Glu, $R_2$ is L-Gln, Y is L-Lys, and B is D-Leu-OH.

12. The compound of claim 1 wherein $A_1$ and $A_2$ are H-Gly, X is L-Met, $R_1$ is L-Glu, $R_2$ is L-Gln, Y is L-Lys and B is L-Leu-$NHCH_3$.

13. The compound of claim 1 wherein $A_1$ and $A_2$ are H-Gly, X is L-Met, $R_1$ is L-Glu, $R_2$ is L-Gln, Y is L-Lys and B is L-Leu-$OCH_3$.

14. The compound of claim 1 wherein $A_1$ and $A_2$ are H-Gly, X is L-Met, $R_1$ is L-Glu, $R_2$ is L-Gln, Y is L-Lys and B is L-Leu-L-Phe-L-Lys-OH.

15. The compound of claim 1 wherein $A_1$ and $A_2$ are H-Gly, X is L-Met, $R_1$ is L-Glu, $R_2$ is L-Gln, Y is L-Lys and B is L-Leu-L-Phe-OH.

16. The compound of claim 1 wherein $A_1$ and $A_2$ are H-Gly, X is L-Met, $R_1$ is L-Glu, $R_2$ is L-Gln, Y is L-Lys and B is L-Leu-L-Phe-D-Lys-OH.

17. A pharmaceutical composition effective for treating schizophrenia, comprising:
(A) a pharmaceutically effective amount of a compound of the formula:

$A_1$-$A_2$-L-Phe-X-L-Thr-L-Ser-$R_1$-Y-L-Ser-$R_2$-L-Thr-L-Pro-L-Leu-Val-L-Thr-B wherein:
(1) $A_1$ and $A_2$ each represent an L-amino-acid residue of the formula $H_2N$-ALK-CO-, wherein ALK is an alkylidene group with 1 to 6 carbon atoms;
(2) X is an amino-acid residue selected from the group consisting of L-Met, L-Met(O), L-Met-($O_2$), and L-Leu;
(3) $R_1$ and $R_2$ each represent one of the amino-acid residues selected from the group consisting of L-Glu and L-Gln;
(4) Y represents an amino-acid residue selected from the group consisting of L-Lys and D-Lys; and
(5) B represents one of the amino-acid- or peptide-moieties selected from L-Leu-OH, D-Leu-OH, L-Leu-L-Phe-OH, L-Leu-L-Phe-L-Lys-OH, L-Leu-L-Phe-D-Lys-OH, L-leucinol and L-MeLeu-OH; and functional derivatives of said compound selected from the group consisting of pharmaceutically acceptable acid addition salts, pharmaceutically acceptable metal salts, aliphatic esters containing up to about eighteen carbon atoms unsubstituted amides, amides substituted with alkyl group (s) having up to about six carbon atoms, N-acyl derivatives wherein the aliphatic carboxylic acid group has from up to about six carbon atoms, and pharmaceutically acceptable metal complexes, and (B) a pharmaceutically effective carrier therefor.

18. The composition of claim 17 wherein $A_1$ is selected from the group consisting of H-Gly and H-L-Ala.

19. The composition of claim 17 wherein $A_2$ is selected from the group consisting of H-Gly and H-L-Ala.

20. The composition of claim 17 wherein B is selected from the group consisting of L-Leu-OH, D-Leu-OH and L-Leu-L-Phe-D-Lys-OH.

21. The composition of claim 17 wherein X is selected from the group consisting of L-Met, L-Met(O), and L-Met(O$_2$).

22. The composition of claim 17 wherein R$_1$ is L-Glu and R$_2$ is L-Gln.

23. The composition of claim 17 wherein Y is L-Lys.

24. The composition of claim 17 wherein A$_1$ and A$_2$ are H-Gly, X is L-Met, R$_1$ is L-Glu, R$_2$ is L-Gln, Y is L-Lys and B is L-Leu-OH.

25. The composition of claim 17 wherein A$_1$ and A$_2$ are H-Gly, X is L-Met(O), R$_1$ is L-Glu, R$_2$ is L-Gln, Y is L-Lys and B is L-Leu-OH.

26. The composition of claim 17 wherein A$_1$ and A$_2$ are H-Gly, X is L-Met(O$_2$), R$_2$ is L-Glu, R$_2$ is L-Gln, Y is L-Lys and B is L-Leu-OH.

27. The composition of claim 17 wherein A$_1$ and A$_2$ are H-Gly, X is L-Met, R$_1$ is L-Glu, R$_2$ is L-Gln, Y is L-Lys and B is D-Leu-OH.

28. The composition of claim 17 wherein A$_1$ and A$_2$ are H-Gly, X is L-Met, R$_1$ is L-Glu, R$_2$ is L-Gln, Y is L-Lys and B is L-Leu-NHCH$_3$.

29. The composition of claim 17 wherein A$_1$ and A$_2$ are H-Gly, X is L-Met, R$_1$ is L-Glu, R$_2$ is L-Gln, Y is L-Lys and B is L-Leu-OCH$_3$.

30. The composition of claim 17 wherein A$_1$ and A$_2$ are H-Gly, X is L-Met, R$_1$ is L-Glu, R$_2$ is L-Gln, Y is L-Lys and B is L-Leu-L-Phe-L-Lys-OH.

31. The composition of claim 17 wherein A$_1$ and A$_2$ are H-Gly, X is L-Met, R$_1$ is L-Glu, R$_2$ is L-Gln, Y is L-Lys and B is L-Leu-L-Phe-OH.

32. The composition of claim 17 wherein A$_1$ and A$_2$ are H-Gly, X is L-Met, R$_1$ is L-Glu, R$_2$ is L-Gln, Y is L-Lys and B is L-Leu-L-Phe-D-Lys-OH.

33. Method for the treatment of schizofrenia in humans, comprising: administering a pharmaceutically effective amount of a compound of the formula:

A$_1$-A$_2$-L-Phe-X-L-Thr-L-Ser-R$_1$-Y-L-Ser-R$_2$-L-Thr-L-Pro-L-Leu-L-Val-L-Thr-B wherein:
(a) A$_1$ and A$_2$ each represent an L-amino-acid residue of the formula H$_2$N-ALK-CO-, wherein ALK is an alkylidene group with 1 to 6 carbon atoms;
(b) X is an amino-acid residue selected from the group consisting of L-Met, L-Met(0), L-Met(0$_2$) and L-Leu;
(c) R$_1$ and R$_2$ each represent one of the amino-acid residues selected from the group consisting of L-Glu and L-Gln;
(d) Y represents an amino-acid residue selected from the group consisting of L-Lys and D-Lys; and
(e) B represents one of the peptides selected from the group consisting of L-Leu-OH, D-Leu-OH, 1-MeLeu-OH, L-Leu-L-Phe-OH, L-Leu-L-Phe-L-Lys-OH, L-Leu-L-Phe-D-Lys-OH and L-Leucinol.

34. The method of claim 33 wherein the compound is administered in a dosage of 1 µg to 1 mg per kg body weight per day functional derivatives of said compound selected from the group consisting of pharmaceutically acceptable acid addition salts, pharmaceutically acceptable metal salts, aliphatic esters containing up to about eighteen carbon atoms, unsubstituted amides, amides substituted with alkyl group (s) having up to about six carbon atoms, N-acyl derivatives wherein the aliphatic carboxylic acid group has from up to about six carbon atoms, and pharmaceutically acceptable metal complexes.

35. The method of claim 33 wherein A$_1$ and A$_2$ are H-Gly, X is L-Met, R$_1$ is L-Glu, R$_2$ is L-Gln, Y is L-Lys, and B is L-Leu-OH.

* * * * *